United States Patent [19]

Yamamoto

[11] Patent Number: 5,712,104
[45] Date of Patent: Jan. 27, 1998

[54] DIAGNOSTIC AND PROGNOSTIC ELISA ASSAYS OF SERUM OR PLASMA α-N-ACETYLGALACTOSAMINIDASE FOR CANCER

[76] Inventor: Nobuto Yamamoto, 1040 66th Ave., Philadelphia, Pa. 19126

[21] Appl. No.: 779,729

[22] Filed: Jan. 6, 1997

Related U.S. Application Data

[63] Continuation-in-part of Ser. No. 478,121, Jun. 7, 1995, Pat. No. 5,620,846, and Ser. No. 618,485, Mar. 19, 1996.
[51] Int. Cl.$^6$ ..................................................... G01N 33/53
[52] U.S. Cl. .......................... 435/7.92; 435/7.1; 435/7.23; 435/7.93; 435/7.94; 435/7.95; 435/18; 436/501; 436/531; 436/813
[58] Field of Search .................... 435/4, 5, 7.1, 7.23, 435/7.9, 7.92, 7.94, 18, 34, 974; 436/501, 531, 813

[56] References Cited

PUBLICATIONS

Yamamoto et al, "Deglycosylation of Serum Vitamin D3-Binding Protein Leads to Immunosuppression in Cancer Patients", *Cancer Research*, vol. 56, No. 12 (1996 Jun. 15), pp. 2827–2831.

*Primary Examiner*—Donald E. Adams
*Assistant Examiner*—Jeffrey Stucker
*Attorney, Agent, or Firm*—Caesar, Rivise, Bernstein, Cohen & Pokotilow, Ltd.

[57] ABSTRACT

Cancerous cells and HIV- and influenza virus-infected cells secrete α-N-acetylgalactosaminidase into blood stream, resulting in deglycosylation of Gc protein. This inactivates the MAF precursor activity of Gc protein, leading to immunosuppression. Thus, α-N-acetylgalactosaminidase activity in patient bloodstream can serve as diagnostic and prognostic index. Antibody-sandwich ELISA method and kits for cancer, HIV and influenza specific α-N-acetylgalactosaminidase as an antigen were developed to detect serum or plasma α-N-acetylgalactosaminidase in cancer and AIDS/HIV-infected and influenza patients and used as a diagnostic/prognostic index.

2 Claims, 5 Drawing Sheets

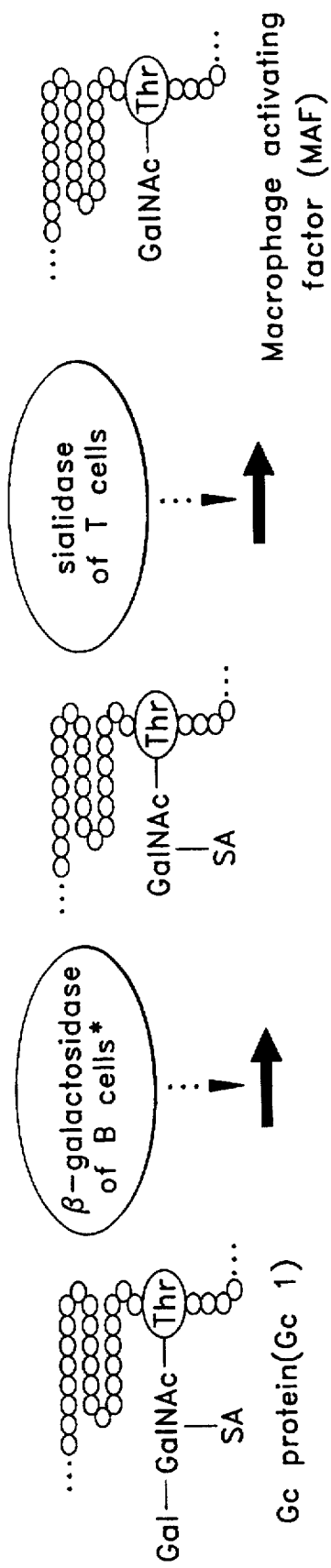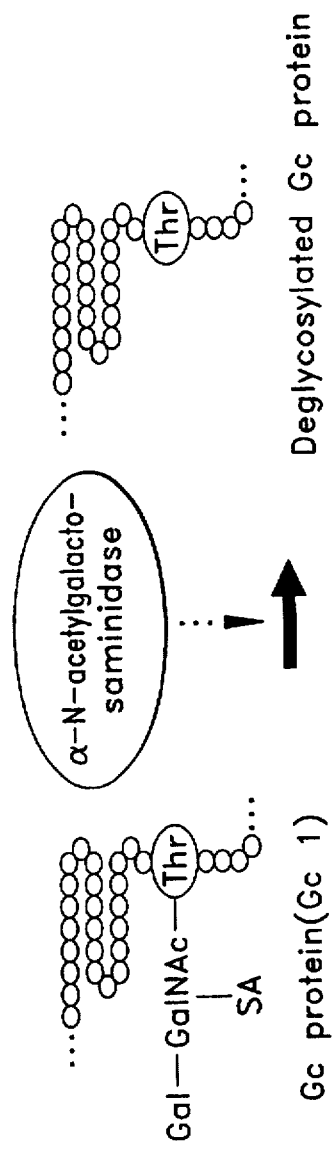
FIG. 1A
FIG. 1B

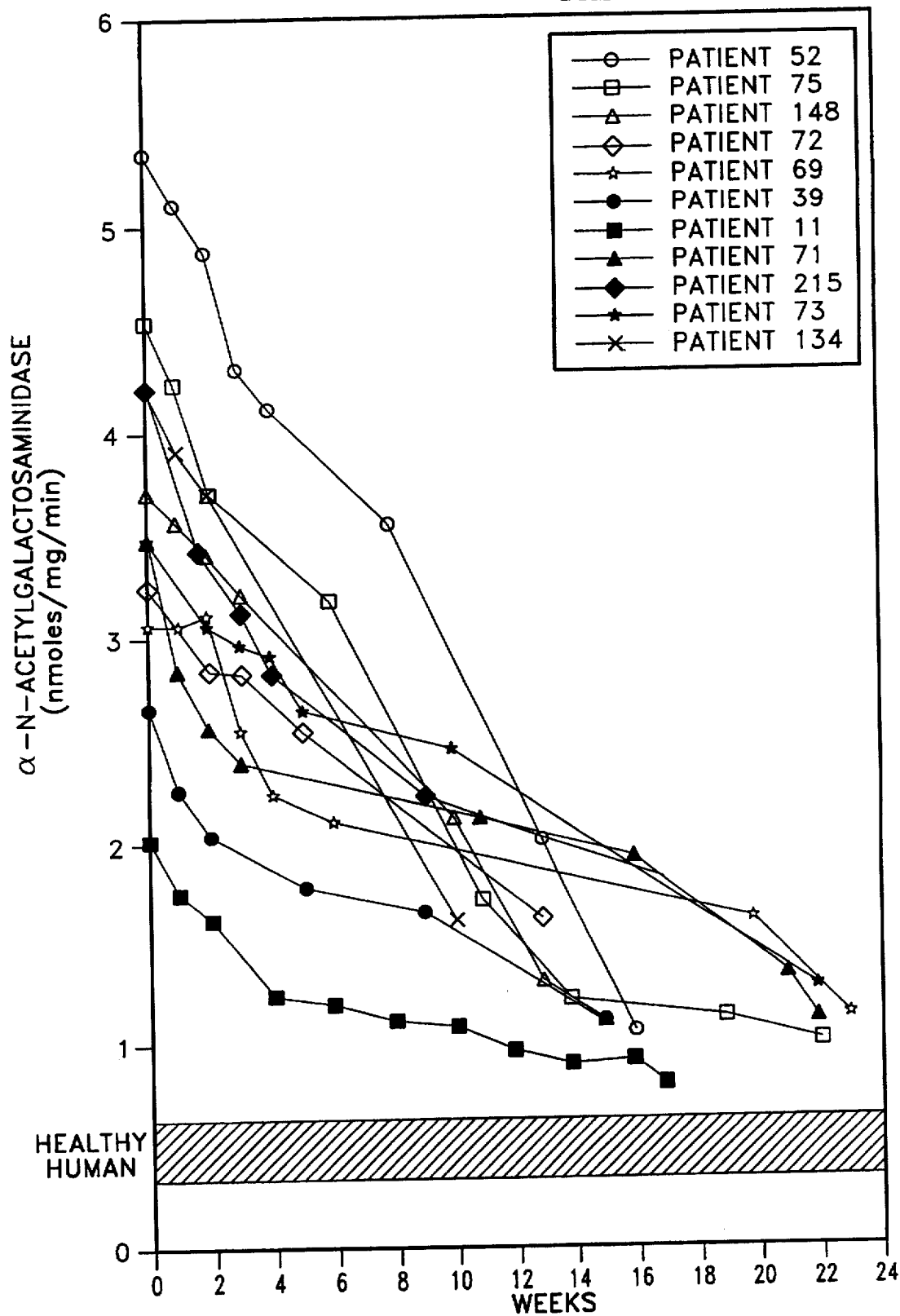

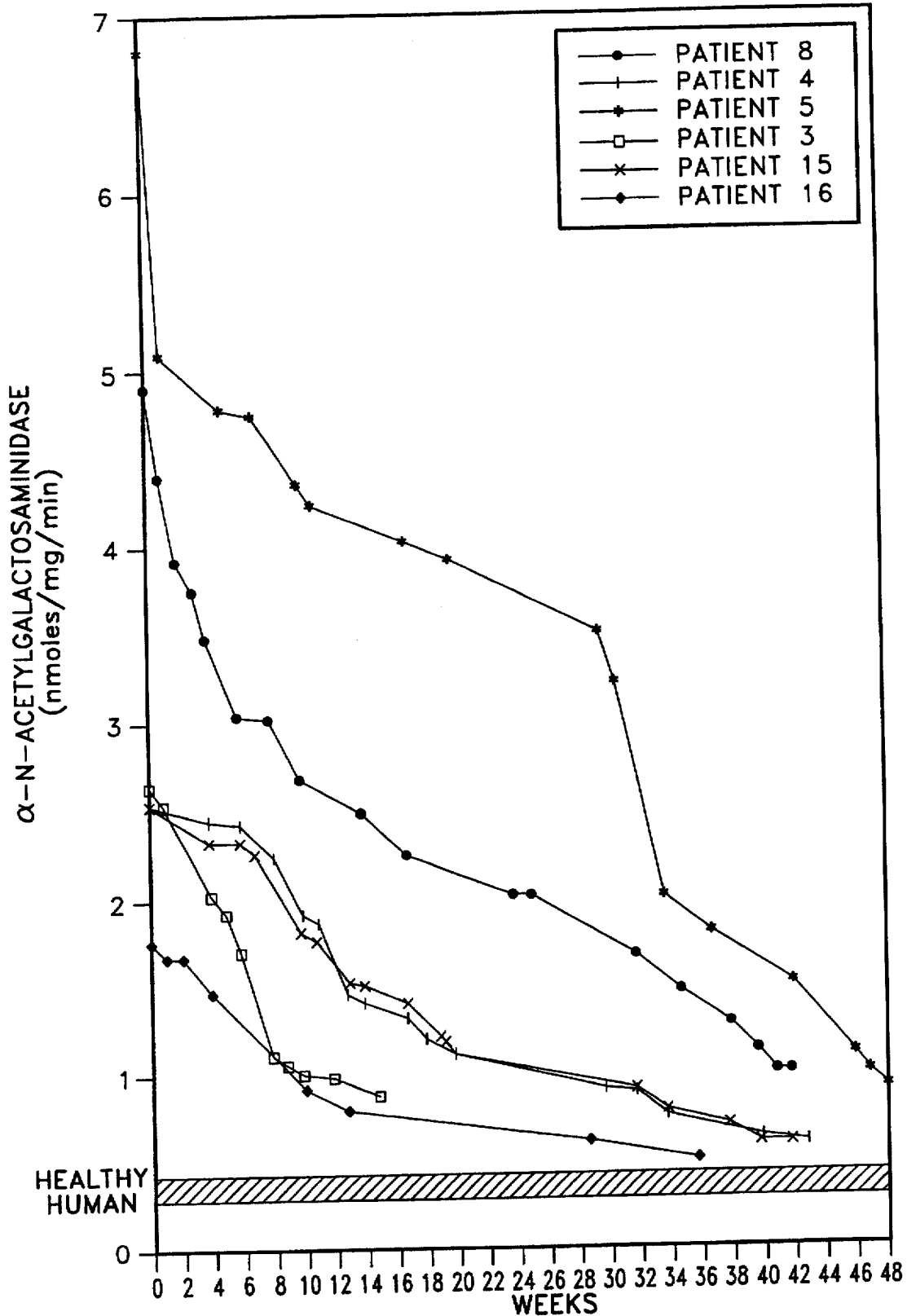

DIAGNOSTIC AND PROGNOSTIC ELISA ASSAYS OF SERUM OR PLASMA α-N-ACETYLGALACTOSAMINIDASE FOR CANCER

RELATED APPLICATIONS

This application is a continuation-in-part application of application Ser. No. 08/478,121 now U.S. Pat. No. 5,620,846 filed Jun. 7, 1995, entitled DIAGNOSTIC AND PROGNOSTIC INDICES FOR CANCER AND AIDS, and continuation-in-part of application Ser. No. 08/618,485 filed Mar. 19, 1996, entitled PREPARATION OF POTENT MACROPHAGE ACTIVATING FACTORS DERIVED FROM CLONED VITAMIN D BINDING PROTEIN AND ITS DOMAIN AND THEIR THERAPEUTIC USAGE FOR CANCER, HIV-INFECTION AND OSTEOPETROSIS, the entire disclosures of which are incorporated by reference herein.

FIELD OF THE INVENTION

This invention relates to diagnostic and prognostic methods utilizing enzyme-linked immunosorbent assay (ELISA) to detect the specific enzyme, α-N-acetylgalactosaminidase that causes immunosuppression, found in the blood stream of cancer, AIDS/HIV-infected and influenza patients.

TABLE OF TERMS

| | |
|---|---|
| Gc protein | Vitamin $D_3$-binding protein |
| MAF | macrophage activating factor |
| GcMAF | Gc protein-derived macrophage activating protein |
| Nag | α-N-acetylgalactosaminidase |
| NagAg | α-N-acetylgalactosaminidase as an antigen |
| ELISA | enzyme-linked immunosorbent assay |

SUMMARY OF THE INVENTION

Vitamin $D_3$-binding protein (Gc protein) is the precursor for macrophage activating factor (MAF). Cancerous cells and HIV- and influenza virus-infected cells secrete α-N-acetylgalactosaminidase into the bloodstream, resulting in the deglycosylation of Gc protein. This inactivates the MAF precursor activity of Gc protein, leading to immunosuppression. Thus, α-N-acetylgalactosaminidase activity in a patient's bloodstream can serve as a diagnostic and prognostic index. An antibody-sandwich ELISA method and kits for cancer, HIV and influenza specific α-N-acetylgalactosaminidase as antigens were developed to detect serum or plasma α-N-acetylgalactosaminidase in cancer, AIDS/HIV-infected and influenza patients and used as a diagnostic/prognostic index.

DESCRIPTION OF THE DRAWINGS

Other objects and many attendant features of this invention will become readily appreciated as the same becomes better understood by reference to the following detailed description when considered in connection with the accompanying drawings wherein:

FIG. 1A and 1B show a schematic illustration of the formation of macrophage activating factor (MAF) and the deglycosylation of Gc protein in a cancer or HIV-infected patient's blood stream, respectively.

FIG. 2A, 2B and 2C show the prognostic utility of serum α-N-acetylgalactosaminidase in accordance with the present invention and the therapeutic effect of GcMAF on adult persons suffering from prostate cancer; the prognostic utility of serum α-N-acetylgalactosaminidase and the therapeutic effect of GcMAF on adult persons suffering from breast cancer; and the prognostic utility of serum α-N-acetylgalactosaminidase and the therapeutic effect of GcMAF on adult persons suffering from colon cancer, respectively.

BACKGROUND OF THE INVENTION

Figure 2B:
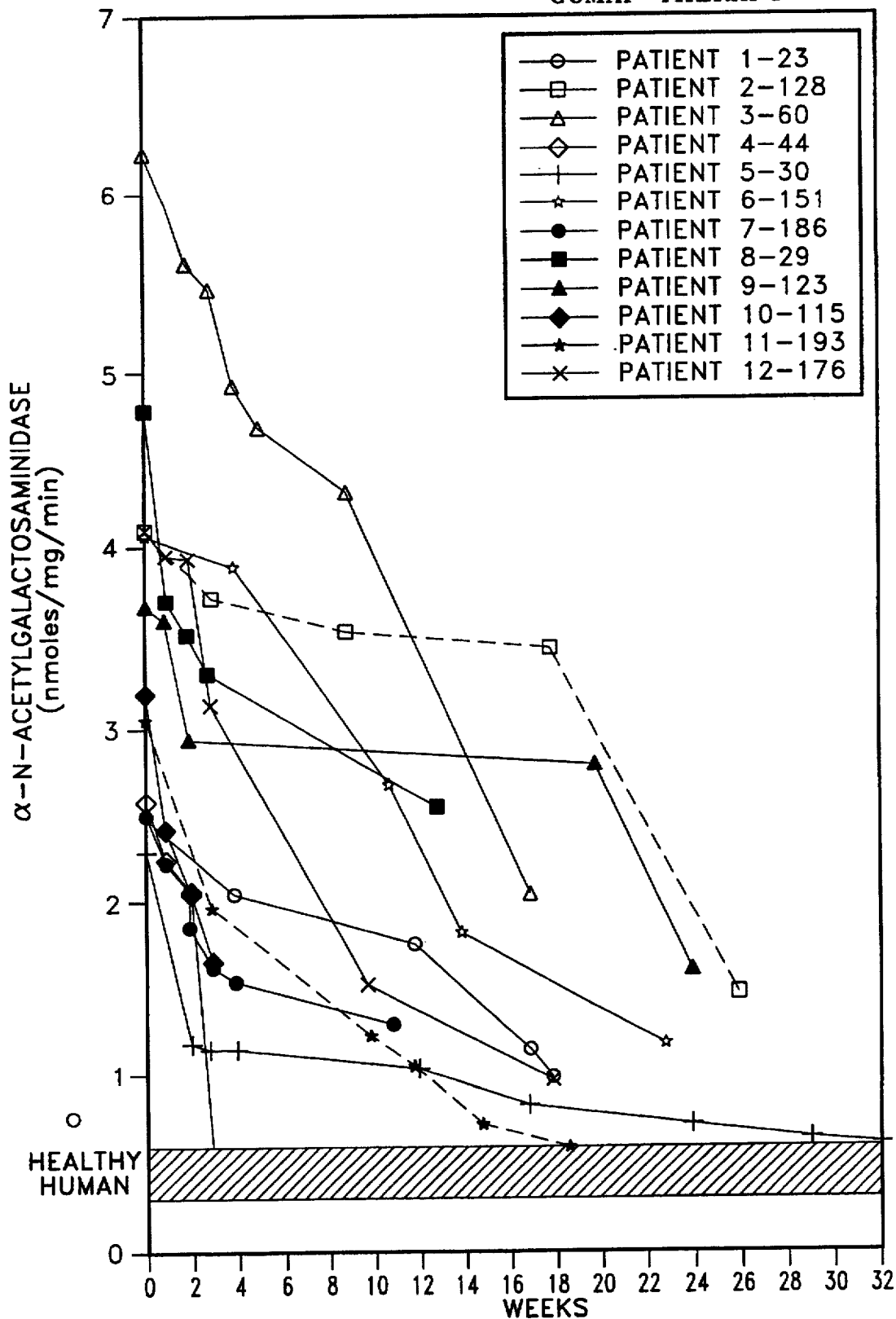

A. Immunosuppression Resulted from Loss of MAF Precursor Activity

Inflammation results in the activation of macrophages. Cellular membrane damage and the inflammatory process result in the release of lysophospholipids. Administration into mice of small doses (5–20 μg/mouse) of lysophosphatidylcholine (lyso-Pc) and other lysophospholipids induced the greatly enhanced phagocytic and superoxide generating capacities of macrophages (Ngwenya and Yamamoto, *Proc. Soc. Exp. Biol. Med.* 193:118, 1990; Yamamoto et al., *Inf. Imm.* 61:5388, 1993; Yamamoto et al., *Inflammation.* 18:311, 1994). This macrophage activation requires the participation of B and T lymphocytes and serum vitamin D binding protein (DBP; human DBP is known as group specific components or Gc). The activation of macrophages by lyso-Pc requires the modification of Gc glycoprotein by the stepwise interaction with β-galactosidase of lyso-Pc-treated B cells and sialidase of T cells, to generate the macrophage activating factor (MAF), a protein with N-acetylgalactosamine as the remaining sugar moiety (FIG. 1a) (Yamamoto and Homma, *Proc. Natl. Acad. Sci. USA.* 88:8539, 1991; Yamamoto and Kumashiro, *J. Immunol.* 151:2794, 1993). Thus, the Gc protein is a precursor for MAF. Incubation of Gc protein with immobilized β-galactosidase and sialidase generates a remarkably high titered MAF (termed GcMAF) (Yamamoto and Homma, *Proc. Natl. Acad. Sci. USA.* 88:8539, 1991; Yamamoto and Kumashiro, *J. Immunol.* 151:2794, 1993; Naraparaju and Yamamoto, *Immunol. Lett.* 43:143, 1994; U.S. Pat. Nos. 5,177,002 and 5,326,749). Administration of a minute amount (10 pg/mouse; 100 ng/human) of GcMAF resulted in a greatly enhanced phagocytic capacity of macrophages. When peripheral blood monocytes/macrophages of over 384 cancer patients bearing various types of cancer were treated in vitro with 100 pg GcMAF/ml, the monocytes/macrophages of all cancer patients were activated for phagocytic and superoxide generating capacities. This observation indicates that patient's monocytes/macrophages are capable of being activated. However, the MAF precursor activity of patient plasma Gc protein was severely reduced in approximately 25% of the cancer patient population. Loss of the MAF precursor activity prevents the generation of MAF (Yamamoto et al., *Cancer Res.* 56:2827, 1996). Therefore, macrophage activation cannot develop in certain cancer patients. Since macrophage activation for phagocytosis and antigen presentation is the first step in the immune development cascade, these cancer patients become immunosuppressed. This may explain at least in part why cancer patients die from overwhelming infection. About 45% of the patients had moderately reduced MAF precursor activities while the remaining (30%) cancer patients had MAF precursor activities similar to those of healthy humans. Lost or reduced precursor activity of Gc protein was found to be due to deglycosylation of plasma Gc protein by α-N- acetylgalactosaminidase detected in a cancer patient's bloodstream (Yamamoto et al., Cancer Res. 56:2827, 1996). Deglycosylated Gc protein cannot be converted to MAF (FIG. 1b). The source of the α-N-acetylgalactosaminidase appeared to be cancerous cells (Yamamoto et al, Cancer Res. 56:2827, 1996). Radiation therapy decreased plasma α-N-acetylgalactosaminidase activity with a concomitant increase of precursor activity. This implies that radiation therapy decreases the number of cancerous cells capable of secreting α-N-acetylgalactosaminidase. Thus, plasma α-N-acetylgalactosaminidase activity has an inverse correlation with the MAF precursor activity of Gc protein (Yamamoto et al., Cancer Res. 56:2827, 1996). Surgical removal of tumors resulted in a subtle decrease in serum α-N-acetylgalactosaminidase activity with the concomitant increase in the precursor activity of serum Gc protein. Serum enzyme analysis of nude mice transplanted with a human oral squamous carcinoma cell line revealed that serum α-N-acetylgalactosaminidase activity is directly proportional to the tumor burden. Thus, α-N-acetylgalactosaminidase activity in a patient's bloodstream can serve as a diagnostic/prognostic index.

When peripheral blood monocytes/macrophages of over 250 HIV-infected/AIDS patients were treated in vitro with 100 pg GcMAF/ml, the monocytes/macrophages of all patients were activated for phagocytic and superoxide generating capacity. However, the MAF precursor activity of plasma Gc protein was severely reduced in about 1/10 of the HIV-infected patient population and approximately 25% of AIDS patients. These patient's plasma Gc protein is deglycosylated by α-N-acetylgalactosaminidase detected in the HIV-infected patient's bloodstream (Yamamoto et al., AIDS Res. Human Retro. 11:1373, 1995). HIV-infected cells appeared to secrete α-N-acetylgalactosaminidase that deglycosylates Gc protein, leading to immunosuppression (Yamamoto et al., AIDS Res. Human Retro. 11:1373, 1995). Similarly, influenza infected cells secrete α-N-acetylgalactosaminidase that deglycosylates Gc protein, leading to immunosuppression. Thus, the α-N-acetylgalactosaminidase activity and MAF precursor activity of Gc protein in a patient's bloodstream can serve as a diagnostic and prognostic index for these virally infected patients.

In my prior two U.S. Pat. Nos. 5,177,002 and 5,326,749, the entire disclosures of which are incorporated by reference herein, as are my above cited journal articles, is disclosed macrophage activating factor, processes for preparing them as well as methods of inducing macrophage activation in a person in need of such activation.

B. The Origin of α-N-acetylgalactosaminidase

Loss of the precursor activity was found to be due to deglycosylation of plasma Gc protein by α-N-acetylgalactosaminidase detected in the cancer patient's bloodstream. The source of the enzyme appeared to be cancerous cells. Ehrlich ascites tumor cells contain a large amount of β-N-acetylglucosaminidase and a small amount of α-N-acetylgalactosaminidase (Yagi et al., Arch Biochem Biophys. 280:61, 1990). Both β-N-acetylglucosaminidase and α-N-acetylgalactosaminidase were detected in tumor tissue homogenates as represented by enzyme activities (about 27.8 and 11.8 nmole/mg/min, respectively) of lung tumor tissue (Yamamoto et al., Cancer Res. 56:2827, 1996). Similar results were also observed with eleven different human tumor tissues including 4 lung, 3 breast, 3 colon and 1 cervix tumors, though the α-N-acetylgalactosaminidase activity varied from 11.8 to 50.8 nmoles/mg/min. A healthy lung tissue studied contained 1.5 nmole/mg/min. Furthermore, serum α-N-acetylgalactosaminidase activity was found in the bloodstream of all types of cancer patients but not in healthy humans. In contrast, the serum/plasma β-N-acetylglucosaminidase activity level of healthy humans is equivalent to those of cancer patients (Yamamoto et al., Cancer Res. 56:2827, 1996). Thus, serum/plasma β-N-acetylglucosaminidase seems to be clinically insignificant. In fact, α-N-acetylgalactosaminidase activity is responsible for the deglycosylation of Gc protein and development of immunosuppression because the Gc protein is O-glycosylated.

Since HIV-infected patients carry α-N-acetylgalactosaminidase activity in their bloodstream that deglycosylates Gc protein (Yamamoto et al., AIDS Res. Human Retro. 11:1373, 1995), this could be the major cause for immunosuppression in HIV-infected/AIDS patients. Cultured HIV-infected cells can secrete α-N-acetylgalactosaminidase into culture medium. When HIV-infected cells were treated with virus inducing agents such as mitomycin C or BUDR (Sato et al., Arch. Virol. 54:333, 1977), an increased α-N-acetylgalactosaminidase activity was detected in culture medium. Thus, this enzyme is likely to be coded by the viral gene. In fact, the HIV-envelope protein, gp120, was found to contain α-N-acetylgalactosaminidase activity. Similarly an influenza virus envelope protein (HA) was found to contain α-N-acetylgalactosaminidase activity. Thus, influenza virus-infected cells can secrete this enzyme into the bloodstream, resulting in the deglycosylation of Gc protein. This would cause immunosuppression in influenza virus-infected patients, leading to an opportunistic secondary infection.

Therefore, serum/plasma α-N-acetylgalactosaminidase activity can serve as a diagnostic/prognostic index in cancer and virus-infected patients, though the enzyme proteins among these diseases are antigenically distinct.

C. Prognostic Significance of α-N-Acetylgalactosaminidase Activity in Blood Stream of Cancer, AIDS/HIV-Infected and Influenza Patients 1. Assay protocol for detection of α-N-acetylgalactosaminidase in blood stream of cancer, AIDS/HIV-infected and influenza patients i) Schematic illustration.

Detection procedure for deglycosylating enzyme of serum Gc protein, α-N-acetylgalactosaminidase, in cancer, AIDS/HIV-infected and influenza patient's blood stream.

Step. I. Stepwise 30 and 70% ammonium sulfate precipitation of plasma or serum:

Serum/plasma (1 ml)+30% and then 70% saturated ammonium sulfate 70% precipitate→dissolved in 50 mM citrate phosphate buffer (pH 6.0)→dialyzed against the same buffer at 4° C. for overnight. The dialysates will be made up to 1 ml in volume.

Step. II. Enzyme assay of α-N-acetylgalactosaminidase

Reaction mixture: 250 µl of the dialyzed sample+250 ml of 50 mM citrate phosphate buffer (pH 6.0) containing 5 µmoles of p-nitrophenyl N-acetyl-α-D-galactosaminide as substrate.

Incubation time: 60 min, terminated by adding 200 µl of 10% TCA. After centrifugation of the reaction mixture, 300 µl of 0.5M Na$_2$CO$_3$ will be added to the supernatant.

Activity measurement: absorbance of amount of released p-nitrophenol will be determined spectrophotometrically at 420 nm with Beckman DU 600 Spectrophotometer and expressed as specific activity unit of nmole/mg/min. Protein concentrations were determined by the Bradford method.

ii) Descriptive enzyme assay procedure for α-N-acetylgalactosaminidase.

Plasma/serum (1 ml) of a healthy human and patients will be precipitated with 70% saturated ammonium sulfate. The ammonium sulfate precipitate will be dissolved in 50 mM citrate phosphate buffer (pH 6.0) and dialyzed against the same buffer at 4° C. The volume of the dialysate will be made up to 1 ml. Ammonium sulfate precipitation also separates the enzyme from product inhibitors. The substrate solution (250 µl) contained 5 µmoles of p-nitrophenyl N-acetyl-α-D-galactosaminide in a 50 mM citrate phosphate buffer (pH 6.0). The reaction will be initiated by addition of 250 µl of the dialyzed samples, kept at 37° C. for 60 min and terminated by adding 200 µl of 10% TCA. After centrifugation of the reaction mixture, 300 µl of 0.5M $Na_2CO_3$ solution will be added to the supernatant. The amount of released p-nitrophenol will be determined spectrophotometrically at 420 nm with a Beckman DU 600 Spectrophotometer and expressed as specific activity unit of nmole/mg/min. Protein concentration were estimated by Bradford method (see U.S. Pat. No. 5,620,846).

2. Prognostic Utility of Serum α-N-acetylgalactosaminidase for therapeutic Effects of GcMAF on Cancer and Virus Infected Patients.

a) Cancer patients: Therapeutic effect of GcMAF on prostate, breast and colon cancer patients.

Macrophages have a potential to eliminate cancerous cells when activated. Administration of GcMAF (100 ng/human) to healthy volunteers resulted in the greatly enhanced activation of macrophages as measured by the 7-fold enhanced phagocytic capacity and the 15-fold increased superoxide generating capacity of macrophages, although GcMAF (100 and 1000 ng/human) showed no signs of any side effects to humans. Various dosages (100 pg to 10 ng/mouse) of GcMAF to a number of mice produced neither ill effects nor histological abnormality in various organs including liver, lung, kidney, spleen, intestine and brain. When patients with various types of cancer were treated with GcMAF (100 ng/week), remarkable curative effects were observed. The efficacy of GcMAF was assessed by serum α-N-acetylgalactosaminidase activity because the serum enzyme level is proportional to the total amount of cancerous cells (tumor burden). Curative effects of GcMAF on prostate, breast and colon cancer are illustrated in FIGS. 2a to 2c. After 25 weekly administrations of 100 ng GcMAF the majority (>90%) of prostate and breast cancer patients exhibited insignificantly low levels of the serum enzyme. A similar result was also observed after 35 GcMAF administrations to colon cancer patients. Similar curative effects of GcMAF on lung, liver, stomach, brain, bladder, kidney, uterus, ovarian, larynx, esophagus, oral and skin cancers including mesothelioma and desmoplastic cancer were observed. Thus, GcMAF appeared to be effective on a variety of cancers indiscriminately. However, GcMAF showed no evidence of side effects in these patients after more than 6 months of therapy. This was also confirmed by blood cell counts profile, liver and kidney functions, etc.

b) Virus infected patients

Treatment of peripheral blood macrophages of AIDS/HIV-infected patients with 100 pg GcMAF/ml resulted in a greatly enhanced macrophage activation (Yamamoto et al., *AIDS Res. Human Ret.* 11:1373, 1995). HIV-infected patients carry anti-HIV antibodies. HIV-infected cells express the viral antigens on the cell surface. Thus, macrophages can preferentially act on the infected cells via Fc-receptor mediated cell-killing/ingestion when activated.

Similarly, GcMAF treatment of peripheral blood macrophages of patients chronically infected with Epstein-Barr virus (EBV) and with herpes virus with 100 ng GcMAF/ml resulted in a greatly enhanced macrophage activation. Like HIV infected T cells, EBV infects lymphocytes (B cells). These enveloped viruses including influenza virus code for α-N-acetylgalactosaminidase and the infected cells secrete the enzyme into blood stream. Thus, the enzyme activity in patient sera can be used as a prognostic index during therapy. When we employed the ELISA assay, each virus species was distinguished because these viral envelope proteins do not cross react serologically. After approximately 35 administrations of GcMAF (100 ng/week) to patients chronically infected with EBV and with herpes virus, the enzyme activity decreased to that of healthy control levels.

DESCRIPTION OF THE ENZYME-LINKED IMMUNOSORBENT (ELISA) ASSAY PROCEDURE FOR α-N-ACETYLGALACTOSAMINIDASE ACTIVITY AS AN ANTIGEN IN BLOOD STREAM OF CANCER, AIDS/HIV-INFECTED AND INFLUENZA PATIENTS

In the immunoassay procedure for the detection of serum or plasma α-N-acetylgalactosaminidase (Nag) as an antigen (NagAg), an antibody-sandwich ELISA kit was prepared.

1. Preparation of antibody. The tumor Nag enzyme was purified from a human lung tumor tissue homogenate and used for immunization of animals (rabbit, goat and mouse). Polyclonal antibodies (goat and rabbit) and monoclonal antibodies against α-N-acetylgalactosaminidase (NagAg) were prepared. Immunoglobulin fraction was purified from antisera or monoclonal ascites fluid using ammonium sulfate (50% saturated) fractionation and DE52 ionic exchange or protein A columns.

2. Conjugation of alkaline phosphatase to antibodies. Dialyze 5 mg/ml monoclonal or polyclonal antibody solution in 0.1M phosphate buffer at pH 6.8 (PBS) overnight at 4° C. Add 100 µl of dialyzed antibody solution (3 mg/ml) to 90 µl of 10 mg/ml alkaline phosphatase (immunoassay grade; Boehringer Mannheim, Indianapolis, Ind.) in a 1.5-ml microcentrifuge tube. Add 5 µl 25% glutaraldehyde and mix gently. Let stand at room temperature. Remove 25-µl samples at time 0, 5, 10, 15, 30, 60 and 120 min and place separate 1.5-ml microcentrifuge tubes. Add 125 µl PBS to each sample, then add 1.1 ml Tris/ovoalbumin solution. Dialyze samples against PBS overnight at 4° C. Test each sample for alkaline phosphatase activity using a direct ELISA to determine which conjugation time yields the most active enzyme conjugation. The best enzyme activity was obtained by the 60 min conjugation time. This optimal conjugation time was used for preparation of a larger amount of alkaline phosphatase-antibody conjugates.

3. Preparation of antibody coated microtiter plates. Using multichannel pipets and tips, dispense 50 µl of polyclonal or monoclonal antibody solution 2 µg/ml in PBSN (PBS containing 0.05% sodium azide) into each well of a microtiter plate (microwell). Wrap the plates in plastic wrap to seal and incubate 2 hrs at 37° C. or overnight at room temperature. Rinse the antibody coated plate by flooding with distilled water more than three times. Fill each well with blocking buffer (PBS containing 0.05% Tween 20, 1 mM EDTA, 0.25% BSA and 0.05% $NaN_3$) dispensed as a stream from a bottle and incubate 30 min at room temperature. Rinse the plate three times with distilled water and remove any residual liquid by gently flicking it face down onto paper towels.

4. Antigen (NagAg) preparation. a) Standard antigen for standard curve. Prepare a standard antigen-dilution series by successive 1:3 dilutions of antigen stock (e.g., the enzyme purified from a lung cancer tissue or egg grown influenza virus lysates) in blocking buffer. The range of dilution spans from 2 to 50 μg/ml.

b) Test antigen. Serum/plasma of cancer, HIV-infected and influenza patients which contains ranging 2 to 50 μg enzyme (NagAg)/ml of patient serum or plasma.

5. Assay: Step I. Add 50-μl aliquots (10 μl serum+40 μl PBSN) of the antigen test solutions (serum or plasma) or the standard antigen dilutions to the antibody coated wells and incubate 2 hrs at room temperature. Rinse plate three times in distilled water. Fill each well with blocking buffer and incubate 10 min at room temperature. Rinse three times with water and remove residual liquid. Step II. Add 50 μl specific antibody-alkaline phosphatase conjugate (typically 25 to 400 ng/ml) and incubate 2 hr at room temperature. Wash plate as in Step I. Step III. Add 75 μl of p-nitrophenyl phosphate (NPP) substrate solution to each well and incubate 1 hr at room temperature. Enzyme activity causes the solution to change color. Color intensity relates to the presence or absence of NagAg. Read the plate on a microtiter plate reader with a 405-nm filter.

Figure 3:
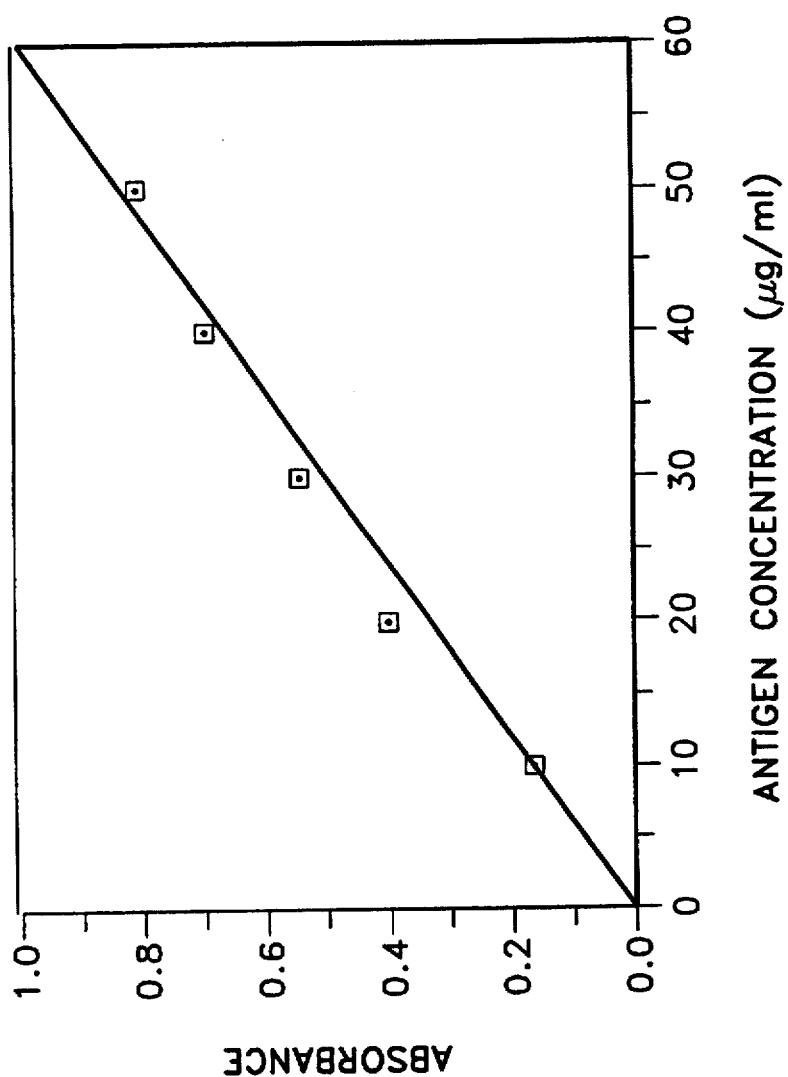
FIG. 3 shows the standard correlation between α-N-acetylgalactosaminidase as antigen concentration and color density for alkaline phosphatase activity of ELISA.

6. Data analysis. I prepared a standard curve constructed from the data produced by the serial dilutions of the standard antigen as shown in FIG. 3. Antigen concentration was plotted on the x axis and absorbance (optical density) of alkaline phosphatase activity on the y axis. Interpolate the concentration of antigen (NagAg) in the test serum sample. Calculate to α-N-acetylgalactosaminidase activity. Since antibodies to cancer, HIV and influenza virus enzymes are specific to the respective enzymes (NagAg), this antibody sandwich ELISA distinguishes individual enzymes as well as the antigen (α-galactosidase) in control. Serum/plasma α-N-acetylgalactosaminidase activity was also expressed as the product of NagAg concentration (μg) and 0.25 nmole/mg/min, because I found that 1 μg of the enzyme (NagAg) in serum has 0.25 nmole/mg/min of the enzyme activity. Table 1 represents the patient enzyme activities computed from ELISA for sera of 16 cancer patients. Similar results were also observed with AIDS/HIV-infected and influenza patients. These ELISA assays for the patient enzyme activities provide are not only sensitive but also economical procedure for diagnosis and prognosis of the diseases.

TABLE 1

Serum α-N-acetylgalactosaminidase activity of cancer patients computed from ELISA.

| Patient No. | Cancer type/site | ELISA Color density | NagAg (μg) | α-N-acetylgalactoeaminidase activity (nmole/mg/min) |
|---|---|---|---|---|
| 1 | Prostate | 0.18 | 9.8 | 2.45 |
| 2 | Prostate | 0.84 | 45.8 | 11.51 |
| 3 | Prostate | 0.49 | 26.7 | 6.75 |
| 4 | Bladder | 0.71 | 41.4 | 10.38 |
| 5 | Prostate | 0.69 | 34.8 | 8.71 |
| 6 | Breast | 0.51 | 30.0 | 7.50 |
| 7 | Breast | 0.82 | 49.4 | 12.36 |
| 8 | Lung | 0.64 | 39.4 | 9.85 |
| 9 | Esophagus | 0.59 | 35.1 | 13.27 |
| 10 | Prostate | 0.48 | 28.3 | 7.07 |
| 11 | Breast | 0.76 | 42.8 | 10.69 |
| 12 | Lung | 0.71 | 38.7 | 9.68 |
| 13 | Prostate | 0.76 | 44.9 | 11.22 |
| 14 | Melanoma | 0.82 | 51.0 | 12.76 |
| 15 | Prostate | 0.44 | 26.1 | 6.53 |
| 16 | Colon | 0.41 | 23.8 | 5.96 |
| Healthy humans† | | 0.09 | 3.9 | 0.97 ± 0.10 |

†Values represent mean ± S.D. of 12 healthy humans.

References Cited

The following references are cited and their entire text is incorporated fully herein as are all references set forth above in the specification.

U.S. PATENT DOCUMENTS

U.S. Pat. Nos. 5,177,001, 5,177,002 and 5,326,749 (Yamamoto).

OTHER PUBLICATIONS

1. Sato, M., Tanaka, H., Yamada, T. and Yamamoto, N., Persistent infection of BHK/WI-2 cells with rubella virus and characterization of rubella variants. Arch. Virology 54:333–343 (1977).

2. Yagi, F., Eckhardt, A. E., and Goldstein, L. J. Glycosidases of Ehrlich ascites tumor cells and ascitic fluid-purification and substrate specificity of α-N-acetylgalactosaminidase and α-galactosidase: comparison with coffee bean α-galactosidase. Arch. Biochem. Biophys. 280: 61–67, 1990.

3. Ngwenya, B. Z. and Yamamoto, N., Contribution of lysophosphatidylcholine treated nonadherent cells to mechanism of macrophage stimulation. Proc. Soc. Exp. Biol. Med. 193:118–124 (1990).

4. Yamamoto, N. and Homma, S., Vitamin $D_3$ binding protein (group-specific component, Gc) is a precursor for the macrophage activating signal from lysophosphatidylcholine-treated lymphocytes. Proc. Natl. Acad. Sci. USA. 88:8539–8543 (1991).

5. Yamamoto, N. and Kumashiro, R., Conversion of vitamin $D_3$ binding protein (Group-specific component) to a macrophage activating factor by stepwise action of β-galactosidase of B cells and sialidase of T cells. J. Immunol. 151:2794–2902 (1993).

6. Yamamoto, N., Kumashiro, R., Yamamoto, M., Willett, N. P. and Lindsay, D. D., Regulation of inflammation-primed activation of macrophages by two serum factors, vitamin $D_3$-binding protein and albumin. Inf. Imm. 61:5388–5391 (1993).

7. Yamamoto, N., Willett, N. P. and Undsay, D. D., Participation of serum proteins in the inflammation-primed activation of macrophages. Inflammation. 18:311–322 (1994).

8. Naraparaju, V. R. and Yamamoto, N., Roles of β-galactosidase of B lymphocytes and sialidase of T lymphocytes in inflammation-primed activation of macrophages. Immunol. Lett. 43:143–148 (1994).

9. Yamamoto, N., Naraparaju, V. R. and Srinivasula, S. M., Structural modification of serum vitamin $D_3$-binding protein and immunosuppression in HIV-infected patients. AIDS Res. Human Ret. 11:1373–1378 (1995).

10. Yamamoto, N., Naraparaju, V. R. and Asbell, S. O. 1996. Deglycosylation of serum vitamin $D_3$-binding protein leads to immunosuppression in cancer patients. Cancer Research. 56:2827–2931.

I claim:

1. A method for detecting α-N-acetylgalactosaminidase in plasma or serum to screen for cancer comprising the steps of:

(a) providing polyclonal or monoclonal antibodies against α-N-acetylgalactosaminidase;

(b) providing a microtiter plate coated with the antibodies;

(c) adding the serum or plasma to the microtiter plate;

(d) providing alkaline phosphatase-antibody conjugates reactive with α-N-acetylgalactosaminidase to the microtiter plate;

(e) providing p-nitrophenyl-phosphate to the microtiter plate; and (f) comparing the reaction which occurs as a result of steps (a) to (e) with a standard curve to determine the level of α-N-acetylgalactosaminidase compared to a normal individual.

2. An antibody-sandwich ELISA kit to screen for cancer by detecting α-N-acetylgalactosaminidase in plasma or serum, the kit comprising:

(a) a microtiter plate coated with polyclonal or monoclonal antibodies specific to α-N-acetylgalactosaminidase;

(b) polyclonal or monoclonal antibody-alkaline phosphatase conjugates reactive with α-N-acetylgalactosaminidase;

(c) p-nitrophenyl-phosphate; and (d) α-N-acetylgalactosaminidase as an antigen standard.

* * * * *